United States Patent
Sheerin et al.

(10) Patent No.: US 11,045,565 B2
(45) Date of Patent: Jun. 29, 2021

(54) PASTEURIZING PAINTS AND METHOD FOR PASTEURIZING PAINTS

(71) Applicant: Columbia Insurance Company, Omaha, NE (US)

(72) Inventors: Robert Sheerin, North Caldwell, NJ (US); David L. Siegfried, Langhorne, PA (US); Wilbur Mardis, Franklin, TN (US); John Ritzke, East Stroudsburg, PA (US); Navin Tilara, Roseland, NJ (US)

(73) Assignee: Columbia Insurance Company, Omaha, NE (US)

( * ) Notice: Subject to any disclaimer, the term of this patent is extended or adjusted under 35 U.S.C. 154(b) by 0 days.

(21) Appl. No.: 16/837,038

(22) Filed: Apr. 1, 2020

(65) Prior Publication Data

US 2020/0230268 A1   Jul. 23, 2020

Related U.S. Application Data

(62) Division of application No. 15/532,577, filed as application No. PCT/US2015/062664 on Nov. 25, 2016, now Pat. No. 10,639,386.

(60) Provisional application No. 62/219,800, filed on Sep. 17, 2015, provisional application No. 62/087,595, filed on Dec. 4, 2014.

(51) Int. Cl.
| | |
|---|---|
| *A61L 2/08* | (2006.01) |
| *A61L 2/04* | (2006.01) |
| *C09D 5/14* | (2006.01) |
| *B65B 55/16* | (2006.01) |
| *B65B 55/14* | (2006.01) |

(52) U.S. Cl.
CPC .............. *A61L 2/081* (2013.01); *A61L 2/04* (2013.01); *C09D 5/14* (2013.01); *A61L 2202/18* (2013.01); *B65B 55/14* (2013.01); *B65B 55/16* (2013.01)

(58) Field of Classification Search
CPC ... A61L 2/081; A61L 2/08; A61L 2/04; B65B 55/14; B65B 55/16; C09D 5/14
See application file for complete search history.

(56) References Cited

U.S. PATENT DOCUMENTS

| | | | | |
|---|---|---|---|---|
| 5,529,749 A | * | 6/1996 | Rinno | B29B 13/08 422/21 |
| 2014/0010930 A1 | * | 1/2014 | Barbeau | A23L 3/01 426/238 |

* cited by examiner

*Primary Examiner* — Timothy C Cleveland
(74) *Attorney, Agent, or Firm* — The H.T. Than Law Group

(57) ABSTRACT

Disclosed herein are methods for pasteurizing architectural coating compositions using heat, radiation or other energy sources without additionally polymerizing the compositions and storing same.

6 Claims, 2 Drawing Sheets

PASTEURIZING PAINTS AND METHOD FOR PASTEURIZING PAINTS

FIELD OF THE INVENTION

This invention generally relates to paints that have been pasteurized to remove or sufficiently reduce the amount of bacteria, fungi, yeasts and/or other biological agents in paints and to method for pasteurizing same.

BACKGROUND OF THE INVENTION

Due to environmental and health concerns, there has been a movement toward reducing the amount of volatile organic compounds (VOCs) in paints, stains, and other coating compositions, which evaporate into the environment upon paint film formation. Additives to paints that facilitate or impart desirable paint properties, such as better film coalescence, better resistance to blocking, better film durability, better physical and chemical scrub resistance, and tougher coatings, among others, also contain VOCs. The evaporation of VOCs often results in undesirable aromas, and exposure to such fumes, particularly in areas that are not well ventilated, remains a health concern. Thus, less volatile or non-volatile additives, as well as colorants, that impart comparable (or superior) properties to the paints have been used to replace higher VOC additives. The quest for low VOC paints or a better "green paint" is discussed in a New York Times newspaper article entitled "The Promise of Green Paint" (Kershaw, Sarah, The New York Times, May 15, 2008, p. F6), which is incorporated herein by reference in its entirety.

The reduction of VOC in paints, stains and other coatings and in additives, however, has produced environmentally friendly paints that are more inviting to bacteria, algae, yeasts, fungi and other biological agents that thrive in an aqueous environment. These biological agents grow and die in paint cans and containers, and often impart an unpleasant odor and render paints unusable for its intended purpose, and can cause viscosity loss, discoloration, gassing, frothing, sedimentation and pH changes. Biological agents also present potential health issues. Certain biological agents, such as algae and molds, may grow on dried paint films covering walls or other substrates.

Biocides have been used in aqueous paints or stains to control biological agents inside cans and containers. Some of the biocides may remain on the dried paint film to control algae and molds. However, there is a need to minimize the amount of biocides in aqueous paints or dried paint films while preventing the unimpeded growth of biological agents.

SUMMARY OF THE INVENTION

Hence, the invention is directed to a method for pasteurizing paints with an energy source, such as heat, gamma ray radiation, other irradiations, electron beam, etc. to kill any biological agents that may have been introduced into the paints before being poured into paint cans or containers and sealed for transportation or storage before the paints are used by the consumers. The present invention is also directed to storing the paint cans and containers in climate controlled environments to discourage the growth of biological agents while in storage.

DETAILED DESCRIPTION OF THE PREFERRED EMBODIMENTS

Figure 1:
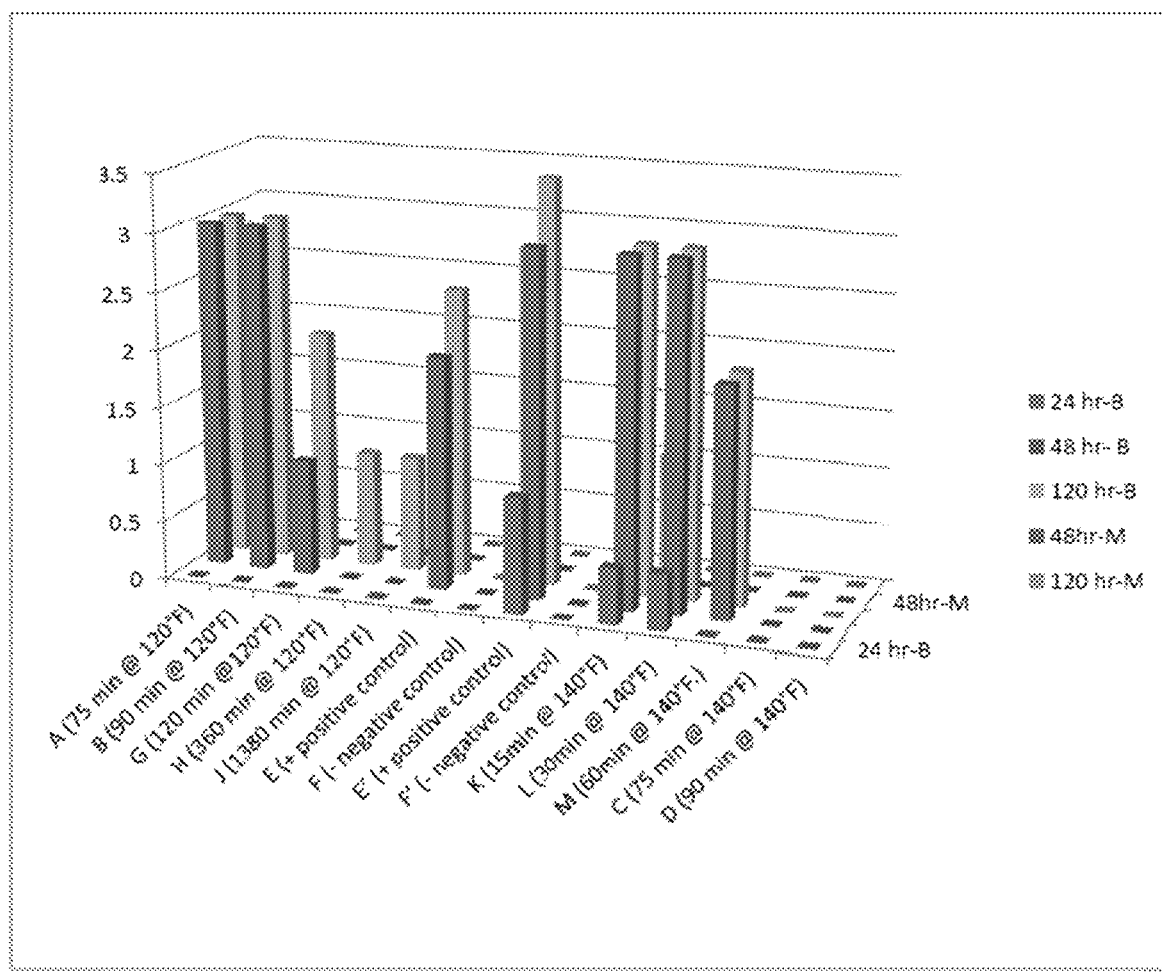
FIG. 1 is a bar graph illustrating the experimental results from Example 7.

As used herein, paint or paints include aqueous or water-based paint compositions, stains or other architectural coatings. Paint film(s) means paint(s) that have been applied on a surface or substrate, and are dried or the latex particles in the paint(s) have cross-linked to form a film.

The energy sources for pasteurization preferably include heat or another thermal source, and radiation including but not limited to irradiation with alpha or gamma rays, microwave rays, electron beams, and any other source of radiation. The present invention is not limited to any particular source of energy as long as that energy source can eradicate biological agents and minimally affect the paints.

Water-based latex architectural coatings, such as paints, stains, other household and industrial coatings and paints, have become more environmentally friendly. This means that modern day architectural coatings have less VOCs in them and have additives and colorants that also have low VOCs. The reduction in VOCs have rendered the architectural coatings more inviting to biological agents, such as bacteria and fungi in the water phase and algae and certain fungi, e.g., molds, in the dried film phase. One solution is to add biocides to the architectural coatings at the latex formation stage, at the pigment dispersion stage, where pigments are dispersed with surfactants, dispersants and water, and/or the let-down stage where the aqueous latex, the pigment dispersion and additives are combined. The paints are then placed in cans and containers for storage and shipping. Colorants, which may contain their own biocides, are added later at the retail stores to achieve the paint colors that the consumers purchased.

While biocides are useful to preserve paints and other architectural coatings and are useful in the dried paint film to help prevent the growth of biological agents, some environmentally conscientious consumers have expressed a desire for biocide-free or biocide-reduced paints. However, without biocide or with reduced biocides biological agents could thrive in paints or paint films.

One aspect of the present invention is to pasteurize the paints and other architectural coatings so that the growth of biological agents is either obviated or limited in the absence of biocide or with reduced biocides. In a preferred embodiment, the paints are pasteurized with an energy source, preferably heat or radiation sources, during the manufacturing process to significantly reduce the population of biological agents, and then stored in containers, such as one-gallon or smaller cans or five-gallon pails. Then paint containers are then stored until sold to the customers. In most situations, the paint containers are shipped to and then stored at paint distribution centers and then shipped and stored at retail stores before being purchased by consumers.

In another embodiment, the paints are pasteurized by the energy source after they are stored in their containers. Entire filled paint containers are pasteurized by subjecting them to the energy source. An advantage of this embodiment is that the empty containers, which may be a source of biological agents, are also pasteurized along with the paints contained therein. Alternatively, the empty containers can be pasteurized separately before they are filled with pasteurized paints.

The duration of the paints' exposure to the energy source should be long enough to substantially eradicate the biological agents.

The following biological agents can be found in paints:
  i. Bacteria: *pseudomonas* species, including *Pseudomonas aeruginosa*; gram negative rod bacteria; *Enterobacter aerogenes*; *Sphingomonas paucimobilis*; etc.
  ii. Yeasts: *Candida lambica* and *Yarrowia lipolytica*, etc.
  iii. Fungi (molds): *aspergillus* species, *acremonium* species, *geotrichum* species and *penicillium* species, etc.

In some of the examples or experiments discussed below, an inoculum comprising the above listed biological agents is introduced into paints or paint containers and the biological agents are allowed to grow. Thereafter, the paints are pasteurized, and the paints are re-tested to determine the residual concentration of biological agents (if any). In other examples or experiments, commercial paints with biocides that were overwhelmed by one or more known biological agents are pasteurized and re-tested to determine whether contaminated paints can be returned to the commercial conditions and be suitable for sale.

*Pseudomonas aeruginosa* or *P. aeruginosa* was found in some contaminated paints. This bacterium is commonly found in wet and warm environments, such as swimming pools and hot tubs. It has been reported by researchers from schools of medicine and public health that *P. aeruginosa* can grow in the range of 25° C. to 42° C. but can be killed at temperature of 60° C. and up to 70° C. for a duration of about 30 minutes. *P. aeruginosa* does not grow but does not die at temperature of 10° C. up to 15° C. or 20° C. These results were reported by A. Tsuji, Y. Kaneko, K. Takahashi, M. Ogawa and S. Goto, "*The Effects of Temperature and pH on the Growth of Eight Enteric and Nine Glucose Non-Fermenting Species of Gram-Negative Rods*," Toho University School of Medicine, Department of Microbiology, J. Microbio. Immunol, Vol. 26(1), 15-24, 1982 at pp. 15-24, which is incorporated herein by reference in its entirety.

Tsuji et al. also reported the effects of heat on the following bacteria.

TABLE 1

| | Bacteria Species | Survival T(° C.)[‡] | Growth T(° C.)[†] | Peak T(° C.) |
|---|---|---|---|---|
| 1 | *E. Coli* | 10-50 | 18-47 | 40 |
| 2 | *K. pneumoniae* | 10-50 | 16-48 | 36 |
| 3 | *S. marcescens* | 10-50 | 19-41 | 35 |
| 4 | *P. aeruginosa* | 10-50 | 25-42 | 37 |
| 5 | *P. cepacia* | 10-50 | 28-37 | 34 |
| 6 | *P. fluorescens* | 10-40[1] | 25-32 | 30 |
| 7 | *P. maltophilia* | 10-50 | 22-39 | 34 |
| 8 | *A. xylosoxidans* | 10-40[2] | 28-37 | 35 |
| 9 | *A. calcoaceticus* | 10-50 | 20-45 | 38 |
| 10 | *A. faecalis* | 10-40[2] | 28-37 | 36 |
| 11 | *F. meningosepticum* | 10-50 | 24-37 | 33 |
| 12 | *Moraxella* | 10-40[3] | 23-35 | 30 |
| 13 | *P. mirabilis* | | 23-44 | 37 |
| 14 | *P. vulgaris* | | 22-41 | 37 |
| 15 | *P. morganii* | | 23-42 | 36 |
| 16 | *P. rettgeri* | | 24-43 | 36 |
| 17 | *P. inconstans* | | 22-45 | 38 |

(*E.* is the genus *Escherichia*; *K.* is the genus *Klebsiella*; *S.* is the genus *Serratia*; *P.* is the genus *Pseudomonas*; *A.* is the genus *Acinebacter*; *F.* is the genus *Flavobacterium*.)
[‡] = survive for at least 6 hours; survival tests conducted at 10-70° C. at increments of 10° C.
[1] = survive at 50° C. for about 1 hour.
[2] = survive at 50° C. for about 4 hours.
[3] = survive at 50° C. for about 2 hours.
[†] = growth tests conducted at 10-50° C. and the time for growth from $10^2$ cells/ml initial concentrations to $10^7$ cells/ml was noted; bacteria growths were observed for 48 hours.

All of the tested bacteria were eradicated at temperature of 60° C. or 70° C. for duration of 30 minutes. No bacteria survived at 60° C. for more than 2 hours. None survived more than 30 minutes at 70° C.

All of the tested bacteria survived at 10° C. but did not grow. Otherwise, they grow at the reported temperature ranges, and the peak or optimal growth temperatures are also reported.

Tsuji et al also reported that at pH from 6.4 to 8.2 has little effect on the growth rate of these bacteria. However, S. Bricha, K. Ounine S. Oulkheir, N. El Haloul and B. Attarassi, "Heat Resistance of *Pseudomonas aeruginosa* in Preparations at the Base of Cucumber, Tomato and Lettuce as Affected by pH and Sodium Chloride," Ibn Tofail University, Morocco, ISPROMS ISSN: 1994-5108, WJBR Vol. 3, Issue 1, at 1-8, reported that at pH of about 2 a heat resistant strain of *P. aeruginosa*'s heat resistance is diminished at temperature of 63° C., but the heat resistance of *P. aeruginosa* at pH of 4.5 and 6 is about the same. Bricha el al. also reported that at low pH sodium chloride salt at 2-6% may protect the bacteria. Bricha et al. is incorporated herein by reference in its entirety.

The present inventive pasteurization method comprises:
  (i) heating (or applying a radiation source to) the paint toward a pasteurization temperature (or pasteurization condition),
  (ii) keeping the exposure time sufficiently long to ensure pasteurization,
  (iii) cooling the paint down to an ambient temperature or lower, and
  (iv) storing the pasteurized paint until being purchased and used by the consumers. Preferably, the eradication in step (i) is up to a 3-log (99.9%) reduction, preferably a 4-log (99.99%) reduction and more preferably a 5-log (99.999%) or more reduction.

Preferably, the energy source is heat and heat is applied, as heated air in ovens, in hot water baths or through heated pipes or vessels, to the biological agents to raise the temperature of the paints to be higher than the growth temperature range of the biological agents and preferably more than about 49° C. or about 50° C. for at least 6 hours for paints substantially without biocide or for at least 2 hours for paints with biocides in an air oven; or about 60° C. for at least about 75 minutes for paints substantially without biocide and for at least about 30 minutes for paints with biocides in an air oven; or about 70° C. for less than 30 minutes, preferably between 1 minute and 30 minutes, preferably between 1 minutes and 15 minutes for paints substantially without biocide, and preferably less than 5 minutes or less than 4 minutes or less than 3 minutes for paints with biocides in an air oven. As shown below, the pasteurization time decreases when hot water baths are used.

Alternatively, other energy source such as radiation as discussed above can be used. In another embodiment, the paints are pasteurized by radiation, e.g., gamma rays or gamma radiation. Paints are pasteurized by absorbing less than or about 15 kilogray (kGy), preferably less than or about 10 kGy, preferably less than about 5 kGy or more preferably less than about 3 kGy.

Preferably the storage of paint in step (iii) includes storing the paint containers in an environment that bacteria, if present, do not grow. As discussed above in Table 1, at 10° C. a large number of bacteria do not grow. Additionally, the temperature growth range of these bacteria is above 15° C., and very few bacteria would grow at temperature at 20° C. Hence, preferably the paints is stored at temperature of 20° C. (68° F.) or lower, more preferably at temperature of 15°

C. (59° F.) or lower, or more preferably at temperature of 10° C. (50° F.) or lower. These preferred storage temperatures can be achieved with conventional air conditioning technology. Additionally, it is preferred that during transportation the paints are also kept at these temperature ranges.

Yeast cells begin to die at temperature greater than 50° C. and most would die at temperatures from about 55° C. to about 60° C. It is well known to bakers that yeasts when added to water that is too warm are killed and the dough won't rise. At temperatures of 10° C. or lower, yeasts would not grow. Yeasts grow in the temperature range from about 27° C. to about 32° C. depending on the species. Hence, yeasts have a similar dormant-growth-death temperature profile as the bacteria discussed above. Hence, yeasts can be eradicated and/or controlled by the inventive pasteurizing method including storage and transportation, described above.

Molds including mildew, fungi, and common molds exist in the same temperature range (and relative humidity) that supports human life. Hence, mold and mold spores are ubiquitous in our environment. Molds can grow in temperatures between 4° C. and 38° C. (40°-100° F.). Below 4° C., molds are in a dormant state and are revived when the temperature warms up with the proper relative humidity. Some molds survive temperature as high as 38° C. or higher. The dormant-growth-death temperature regime for several molds and spores has been reported, as shown below. See http://www.thermapure.com/envinmental-services/mold/.

TABLE 2

| Mold species | Lethal T(° C.) | Duration (min) |
|---|---|---|
| Alternarie altermata | 63 | 25 |
| Aspergillus fumigatus | 65 | 30 |
| Aspergillus niger | 63 | 25 |
| Chaetomium globosum | 57 | 10 |
| Cladosporium herbarum | 50 | 10 |
| Stachybotrys chartarum | 60 | 30 |

While some lethal temperatures are slightly higher than 60° C. for some of the mold discussed above, the time duration to kill is significantly shorter. The present inventors have discovered that at 60° C. but for longer time duration, most molds can be killed. Hence, molds can be eradicated and/or controlled by the same inventive pasteurizing method including storage and transportation, described above.

On the other hand, the heat or radiation treatment should not exceed the temperature/radiation level and duration that would initiate additional polymerization or other deleterious effects within the aqueous paint. Latex particles due to the added heat or radiation energy can cross-link to each other while in solution thereby producing larger latex particles that can negatively affect the quality of the paint film. In some of the examples discussed below, the present inventors have shown that the inventive pasteurization process does not appreciably alter the property of the paints or the paint films.

The inventive pasteurization method may include flash pasteurization, where paint is heated to a relatively higher temperature but for a shorter time period. Flash pasteurization typically takes place immediately after the paint is produced or as the last step in production at the factory before it is stored in containers. Paint can be heated in a heating coil for maximum heat transfer for the requisite time and is then quickly cooled, e.g., with forced convection over cooling fins, to remove the heat. In one example, the paint is heated to a range of about 71° C.—about 74° C. (160° F.-165° F.), preferably about 71° C.—about 73° C. (160° F.-163.5 F), more preferably about 71.5° C. —about 72° C. (161° F.-162° F.) for less than about 4 minutes or less than about 3 minutes, preferably less than about 2.5 minutes, more preferably less about 2 minutes or about 1.5 minutes.

The above method has been used on tainted paints, i.e., paints that could not be commercialized due to biological agent contamination. The heat treatment sufficiently removed the biological agents and the formerly tainted paints could return to the warehouse/distribution center. Tainted paints that are already stored in containers can be pasteurized in an air oven or in a heated bath of water or other liquids. As discussed herein, commercial paints contain biocides added during the manufacturing process.

EXAMPLES

Example 1

Pint size paint cans containing a commercial premium interior flat paint that contains a customary amount of biocides and was contaminated with various bacteria as identified using a dip slide test, which is a hygiene contact slide used to assess the microbiological contamination of surfaces or fluids. Suitable dip slide tests for hygiene monitoring include a plastic two-side testing device commercially available as Difco™ Hycheck™ Yeasts and Molds with TTC (triphenyl tetrazolium chloride as a redox indicator) from Becton Dickenson. These hygiene contact slides are used to assess the microbiological contamination of paints in all examples. Side 1 of a two-sided plastic paddle (aka contact slide) attached to the closure top for the plastic vial is coated with a pink agar recommended for the selective isolation of yeasts and molds (fungal contamination) from environmental materials and foodstuffs. Side 2 is coated with a clear colorless agar medium recommended for microbial limits testing to give a total aerobic bacterial count. Bacterial colony growth is checked after 24, 48 and 72 hours or longer incubation at 30° C., discussed in literature insert supplied with slides and incorporated by reference in its entirety. Testing by this technique does not differentiate types of bacteria, but rather shows all bacteria that are present, and in the case of this contaminated commercial paint, the bacteria have overwhelmed the biocides. The units for the dip slide or Hycheck™ tests are indicative of the number of bacteria or yeasts/molds colonies. Level 1 has about $10^3$ colonies; level 2 has about $10^4$ colonies; level 3 has about $10^5$ colonies; and level 4 has about $10^6$ colonies. The colonies are not actually counted, but are estimated based on comparisons to photographs/pictures provided by the manufacturers. Bacteria are rated level 1, 2, 3 or 4 (max), and molds/yeasts are rated level 1, 2 or 3 (max).

The contaminated paint cans were submerged in a hot water bath set at 67° C. The temperature of the paints was measured by a digital thermometer. The lag time, i.e., the time for the temperature inside the paint can(s) to reach a steady state of about 65.5° C., which is slightly below the hot water bath's temperature, was recorded. These paint cans were then incubated at 30° C. for 72 hours to check for bacterial growth. Bacterial growth was checked after 24, 48 and 72 hours.

| Sample | Time in Bath, hr:min @ 67° C. | Lag Time, hr:min | Pasteurized Time, minutes @ 65.5° C. |
|---|---|---|---|
| A | 0:0 | 0:0 | 0 (control) |
| B | 1:52 | 1:15 | 37 minutes |
| C | 1:30 | 1:15 | 15 minutes |
| D | 1:45 | 1:15 | 30 minutes |
| E | 2:15 | 1:15 | 60 minutes |

Control paint A experienced significant bacterial growth. Samples B-E had no bacterial growth after 24 hours and after 72 hours. No sample exhibited mold/yeast growth. To determine whether the pasteurization affected the physical properties of aqueous paints and paint films, a contaminated sample was compared with a pasteurized sample that has been heated for 60 minutes in the same bath excluding lag time. The results are produced below.

| Property | Contaminated Paint | Pasteurized Paint |
|---|---|---|
| Viscosity (KU) | 101.2 | 101.1 |
| Viscosity (ICI) | 1.396 | 1.333 |
| Gloss 60° | 2.3 | 2.3 |
| Gloss 85° | 2.6 | 2.7 |
| Flow Leveling, 1(worst)-10(best) | 6 | 6 |
| Blocking, 1-5(best) | 5 | 5 |
| Water Sensitivity, 1-5(best) - 1 min | 2 | 2 |
| Water Sensitivity - 2 min | 1 | 1 |
| Water Sensitivity - 3 min | 1 | 1 |
| Water Stain, 1-5(best) | 3.5 | 3.5 |
| Scratch Wet Adhesion, 1-5(best) - 1 min | 4 | 4 |
| Tape Wet Adhesion, 1-5(best) - 2 min | 5 | 5 |
| Tape Wet Adhesion - 5 min | 5 | 5 |
| Tape Wet Adhesion - 10 min | 5 | 5 |
| Scrub cycles, initial/complete break in film | 385/529 | 345/465 |
| Scrub cycles to remove proprietary carbon black stains | 23.0/62.0 | 23.0/61.0 |
| Sag, mils | 12 | 12 |

The wet and dried properties of the contaminated paint and the pasteurized (formerly contaminated) paint are very comparable, except for a small drop in the scrub test. Hence, the inventive pasteurization did not negatively affect the paint. The pasteurization also significantly reduced the odor caused by the contamination.

Example 2

Six vials, each containing 21.5 grams of contaminated paint used in Example 1, were pasteurized in a hot water bath maintained at 71° C. At this relatively small volume, the lag time or time to reach the pasteurized temperature was 2 minutes. The vials were pasteurized for different amount of time, i.e., 1, 2, 4, 8, 16 and 32 minutes excluding lag time or 3, 4, 6, 10, 18 and 34 minutes including lag time. After pasteurization, the vials were immediately submerged in a cold water bath at 12° C. to stop the pasteurization. All six vial samples tested negative for bacterial growth after 72 hours of incubation at 30° C. The control sample tested positive. All samples tested negative for mold and yeast.

Example 3

The results from Example 2 indicated that a short duration of 3 minutes including lag time was sufficient to eradicate the bacteria. This Example explored shorter time durations. Another six vials each containing 21.5 grams of the same contaminated paint were pasteurized with three at 63° C. for 1, 2 and 4 minutes including lag time and three at 71° C. at 0.75, 1.5 and 3 minutes including lag time. The sample pasteurized at 71° C. for 3 minutes duplicates the shortest pasteurized time from Example 2. These six samples and a control were applied to substrates and incubated for 48 hours at 30° C. Digital photographs after the incubation show that pasteurization at 71° C. for 3 minutes killed most of the bacteria and pasteurization at 63° C. for 2 and 4 minutes also killed a significant amount of bacteria.

Example 4

Since commercial paints are sold mostly in gallon-size cans or five-gallon tubs, the present inventors also conducted experiments with the larger paint containers. The heat transfer coefficient of paint is relatively high and the heat capacitance of air in commercial ovens is much lower than that for water thereby causing significant lag time for the paints to reach the heating/pasteurizing temperature from ambient or initial temperature. Individual gallon size paint cans of contaminated commercial paint were heated in an air oven at 80° C. for 5½ hours. The paint temperature only reached 67° C. This means that the paint has not yet reached its steady state oven temperature, and the thermal energy from the oven was not sufficient after 5½ hours to bring the temperature of the paint to the temperature of the oven.

Example 5

Additional experiments were conducted to determine the lag time for heating a box containing four 1-gallon paint cans of the contaminated commercial paints, which tested positive for bacteria by Hycheck incubation, arranged in a 2×2 pattern to reach pasteurizing temperature in an air oven. Boxes of four paint cans are typically sold to and by retail stores. The present inventors discovered that the lag time may be up to 7½ hours for the temperature of the paint inside the cans to reach target pasteurizing temperature of about 60° C. In one example, with an oven air temperature holding at 80.6° C. and after 7 hours and 39 minutes, the air temperature between the cans was 61.8° C. and the paint temperature in the middle of the can was 54.6° C. In another example, with an oven air temperature at about 100° C. and the temperature on top of the cans at 99.2° C. after about 72 hours, the air temperature between the cans was 73.4° C. and the paint temperature in the middle of the can was 67.6° C.

Even though the two samples from Example 5 did not reach their steady state air oven temperature targeted for pasteurization, the heat treated paints were tested for bacterial growth using the Hycheck contact slide incubated at 30° C. for 48 hours and tested negative for bacteria. Example 5 shows that the heat energy used to bring up the paint temperature from ambient toward air oven temperature was sufficient to eradicate the bacteria, even though the paint sample did not reach the targeted pasteurization temperature of 60° C. This result is unexpected in view of the teachings from Tsuji et al, supra.

Example 6

Boxes containing four one-gallon cans of the commercial contaminated paint were heated in the air oven similar to Example 5.

|  | Oven T(° C.) | Paint T(° C.) | Time in Oven | Time at Oven Temperature | Bacteria and Mold/Yeast after Incubation |
|---|---|---|---|---|---|
| Control |  |  |  |  | yes |
| Sample 1 | 60 | 60 | 41.5 hrs | about 10 hrs | none |
| Sample 2 | 70 | 64.6 | 16.75 hrs | n/a | none |
| Sample 3 | 70 | 68.3 | 24.5 hrs | n/a | none |

Paint Properties

|  | Viscosity (KU) | Viscosity (ICI) | Dry Film 85° Sheen | Dry Film 60° Gloss |
|---|---|---|---|---|
| Control | 95.3 | 1.183 | 4.3 | 2.5 |
| Sample 1 | 95.6 | 1.362 | 4.2 | 2.5 |
| Sample 2 | 95.6 | 1.262 | 4.2 | 2.5 |
| Sample 3 | 95.9 | 1.225 | 4.0 | 2.5 |

Except for a slight increase in the ICI viscosity in the aqueous paint, the dry film properties and the KU viscosity did not significantly change.

Based on Examples 1-6 and more specifically Example 5, the present inventors concluded that it may not be necessary to bring the temperature of the paints to a steady state pasteurizing temperature and hold for a certain amount of time in order to eradicate the bacteria.

Example 7

Paints with substantially no biocides were made and inoculated with an inoculum comprising various bacteria and molds from THOR CHEMIE GMBH. Glass vials with caps containing about 52 grams of the inoculated biocide free paints were pasteurized at 49° C. (120° F.) and 60° C. (140° F.) in a heated air oven for varying time periods, as reported below. Two controls were used: a positive inoculated control and a negative control which was not inoculated. Dip slide tests for bacteria were conducted after 24, 48 and 120 hours of incubation and dip slide tests for molds were conducted after 48 and 120 hours incubation.

| Sample (time @ T° F.) | 24 h-B | 48 h-B | 120 h-B | 48 h-M | 120 h-M |
|---|---|---|---|---|---|
| A (75 min @ 120° F.) | 0 | 3 | 3 | 0 | 0 |
| B (90 min @ 120° F.) | 0 | 3 | 3 | 0 | 0 |
| G (120 min @120° F.) | 0 | 1 | 2 | 0 | 0 |
| H (360 min @ 120° F.) | 0 | 0 | 1 | 0 | 0 |
| J (1380 min @ 120° F.) | 0 | 0 | 1 | 0 | 0 |
| E (+positive control) | 0 | 2 | 2.5 | 0 | 0 |
| F (−negative control) | 0 | 0 | 0 | 0 | 0 |
| K (15 min @ 140° F.) | 0.5 | 3 | 3 | 0 | 1 |
| L (30 min @ 140° F.) | 0.5 | 3 | 3 | 0 | 0 |
| M (60 min @ 140° F.) | 0 | 2 | 2 | 0 | 0 |
| C (75 min @ 140° F.) | 0 | 0 | 0 | 0 | 0 |
| D (90 min @ 140° F.) | 0 | 0 | 0 | 0 | 0 |
| E' (+positive control) | 1 | 3 | 3.5 | 0 | 0 |
| F' (−negative control) | 0 | 0 | 0 | 0 | 0 |

The data shows that pasteurization at 120° F. is effective against bacteria and mold growth, but some bacteria were present after 120 hours of incubation at 30° C. Pasteurization at 140° F. for between 60 minutes and 75 minutes is effective for both bacteria and mold. The data also shows that pasteurizing at 140° F. takes less time than pasteurizing at 120° F. The negative controls show that there was no background or other contamination in the experiments and the positive controls show that bacteria would be present without pasteurization. The data also suggests strongly that flash pasteurization can be realized with even higher pasteurizing temperature, preferably below polymerization temperature of the latex particles, for a very short time, as discussed above. The data from Example 7 is graphed as shown in FIG. 1.

Example 8

Commercial paints with conventional biocides that were contaminated were tested in glass vials. Each glass vial holds about 52 grams of the contaminated commercial paints. The vials were pasteurized at 49° C. (120° F.) and 60° C. (140° F.) in a heated air oven, cooled and incubated similar to those in Example 7. The results are as follows:

| Sample (time @ T° F.) | 24 h-B | 48 h-B | 120 h-B | 48 h-M | 120 h-M |
|---|---|---|---|---|---|
| A (120 min @ 120° F.) | 0 | 0 | 0 | 0 | 0 |
| B (360 min @ 120° F.) | 0 | 0 | 0 | 0 | 0 |
| C (1380 min @ 120° F.) | 0 | 0 | 0 | 0 | 0 |
| D (15 min @ 140° F.) | 0 | 4 | 4 | 0 | 0 |
| E (30 min @ 140° F.) | 0 | 0 | 0 | 0 | 0 |
| F (60 min @ 140° F.) | 0 | 0 | 0 | 0 | 0 |
| G(+positive control) | 0 | 4 | 4 | 0 | 0 |

Figure 2:
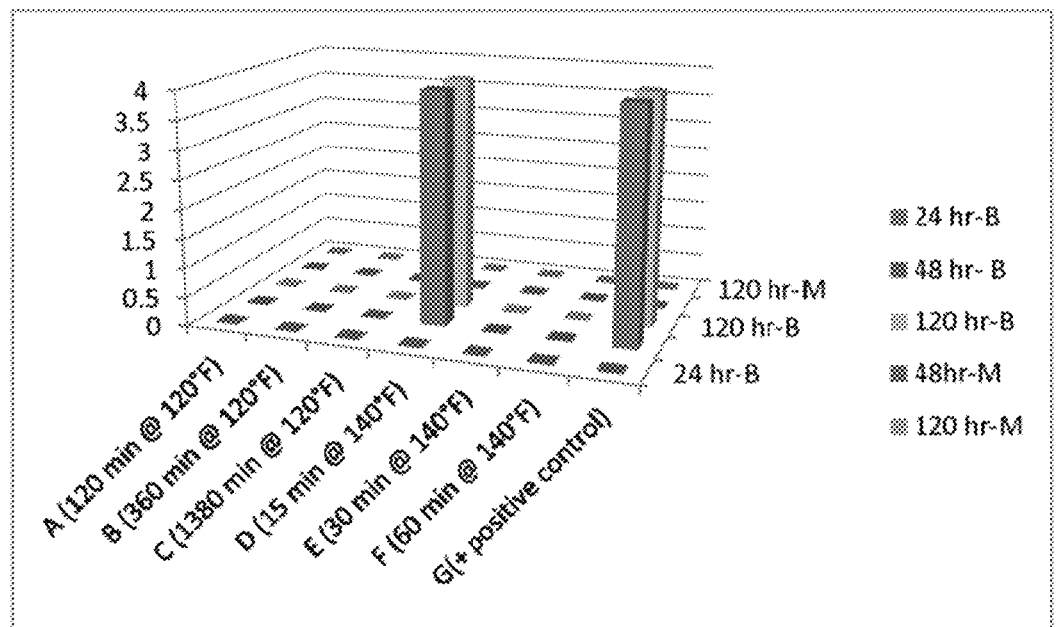
FIG. 2 is a bar graph illustrating the experimental results from Example 8.

Example 8 shows that with biocides in the paint the pasteurized time and temperature can be reduced. Heating at 120° F. for 2 hours (120 minutes) is sufficient to reduce bacterial and mold growth, and heating at 140° F. for 30 minutes is sufficient to reduce bacterial and mold growth. The data from Example 8 is graphed as shown in FIG. 2. Compared to Example 7, the biocides that were overwhelmed by the bacteria and/or mold are reactivated when heated and combined with the pasteurization provide a synergistic effect.

Example 9

Commercial paints with conventional biocides that were contaminated were tested in ½ pint cans containing about 270 grams of paint. The cans were heated in an air oven at 60° (140° F.) for a number of hours to determine whether the overwhelmed biocides can be revived. Samples were heated for 3 hours, 6 hours, 16.5 hours and 25 hours. A positive control, i.e., with additional inoculation, and a negative control, i.e., without additional inoculation, were also checked for bacterial growth. Both controls exhibit significant bacterial growth (4 units) after being incubated for 48 hours, 72 hours and 144 hours. None of the pasteurized sample shows any bacteria growth after 24 hours, 48 hours, 72 hours and 144 hours of incubation. No mold was detected in the pasteurized samples or the controls after being incubated for 48 hours, 72 hours and 144 hours.

The pasteurization regime for paints with biocides gathered from Examples 1-9 can be described as follows. The data is selected in part based on the relative small sizes of the paint samples.

| Time (minutes) | Temperature ° C. | Source |
|---|---|---|
| 3 | 71 | Exs. 2 & 3 |
| 15 | 65 | Ex. 1 |
| 30 | 60 | Ex. 8 |
| 120 | 49 | Ex. 8 |

Figure 3:
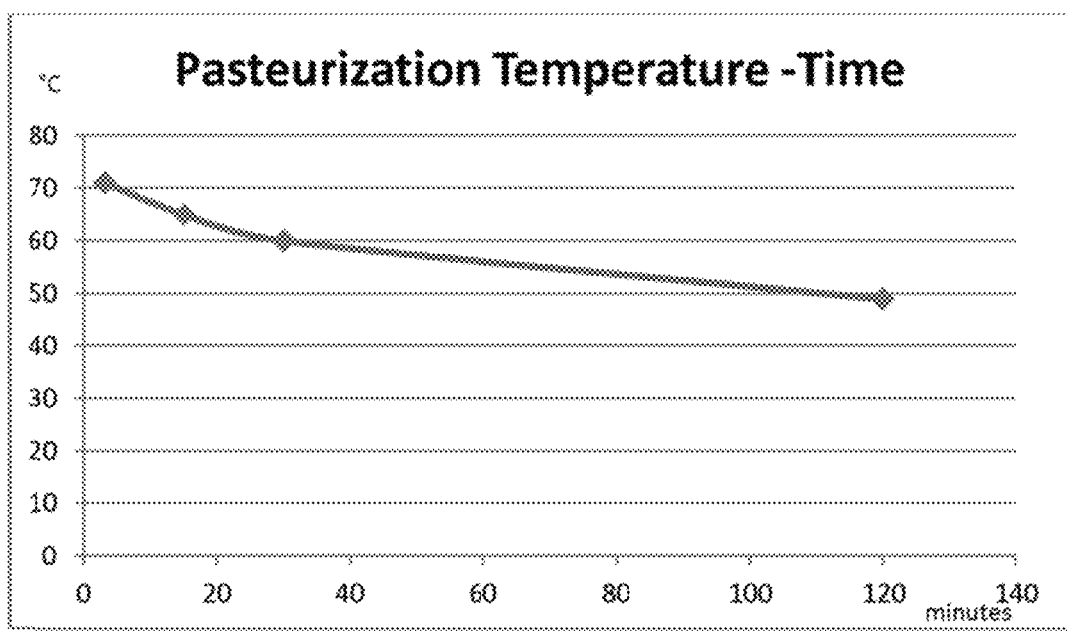
FIG. 3 is an X-Y graph showing a relationship between pasteurizing temperature and pasteurizing time duration.

The pasteurization time-temperature relationship graph is shown in FIG. 3. It is noted that the time duration can be longer than the time reported in this Table as shown in the Examples above, and could be less, e.g., 25% less than the reported time. The graph in FIG. 3 can also be presented on a semi-log graph, i.e., $\log_{10}$(Temperature) vs. time. This table also shows feasibility of flash pasteurization, discussed above.

The pasteurization regime for paints without biocides gathered from Examples 1-9 can be described as follows.

| Time (minutes) | Temperature ° C. | Source |
|---|---|---|
| 75 | 60 | Ex. 7 |
| 360 | 49 | Ex. 7 |

It is noted that the time duration can be longer than the time reported in this Table as shown in the Examples above, and could be less, e.g., 25% less than the reported time.

Example 10A

Commercial paints with conventional biocides that were contaminated were pasteurized with gamma ray radiation. Gallon sized cans were exposed to a various level of gamma radiation, i.e., 3, 5, 10 and 15 KG (kilogray). Some cans were treated with heat at 45.5° C. (114° F.) and at 74.4° C. (166° F.) for comparison, discussed further below in Example 10B. The present inventors discovered that gamma radiation is effective against biological agent contamination while the controls show growth, as shown in the Table below. Additionally, high shear and low shear viscosities (measured in KU and poise) are affected by the radiation. The tint strength is decreased more with heating than with gamma radiation. The contrast ratio is substantially unchanged. Heat and gamma radiation appear to have increased the foam in the paint sample, i.e., pasteurization may have negatively affected the defoamer additive with the gamma radiation having a greater effect.

gamma (γ) level is measured in kilogray (KGy), which is a SI unit equivalent to 1,000 Joules absorbed by 1 kg of matter; the amount of radiation absorbed by the paints relates to the strength of the source of radiation, the distance between the source and the paints and the time duration of exposure.

bacteria levels are checked by dip slide tests (Hychecks) discussed above after a 72 hour inoculation at 30° C.

WPG is the weight (lbs.) per gallon of paint

Viscosity is measured in KU or Krebs Units; ICI viscosity is measured in poise

Gloss and sheen are paint finishes discussed in commonly owned U.S. Pat. No. 8,507,579, which is incorporated by reference herein in its entirety Tint is % tint strength, which is defined as a measure of how well titanium dioxide can add whiteness to a tinted paint, described in commonly owned U.S. patent application Ser. No. 14/531,354 "Additives for Improved Hiding and Painting Compositions Containing Same" filed on 3 Nov. 2014, incorporated herein by reference in its entirety.

Contrast ratio is the ratio of the Y value of the paint over the painted black region divided by the Y value of the paint over the painted white region, and described in Ser. No. 14/531,354.

Foam is the time in seconds for the foam to dissipate or disappear.

Example 10B

In sample 12, a pallet of paints was heated in an air oven at 75° C. (167° F.) for 24 hours, then the oven temperature was increased to 80° C. and again to 85° C. at 24.5 hours. A pallet contains 27 boxes of 4-gallon size cans arranged in three rows of 9 boxes. The temperature of 45.5° C. (114° F.) was measured at a center can after 28 hours. In sample 13, the pallet was broken down to individual rows of 9 boxes, which were separated so that oven air could circulate among the boxes. After 21 hours, the temperature of 74.4° C. (166° F.) was measured after 21 hours.

|  | γ level | Bact. | WPG | Visco. | ICI | pH | Gloss | Sheen | Tint | C/R | Foam |
|---|---|---|---|---|---|---|---|---|---|---|---|
| Control | 0 | 2 | 11.12 | 94.1 | 1.25 | 8.31 | 2.5 | 4.5 | 100.52 | 0.967 | 17 |
| 1 | 3 | 0 | 11.08 | 93.5 | 1.246 | 8.32 | 2.6 | 4.2 | 100.52 | 0.956 | 45 |
| 2 | 3 | 0 | 11.09 | 91.9 | 1.212 | 8.32 | 2.7 | 4.7 | 100.46 | 0.950 | 27 |
| 3 | 5 | 0 | 11.05 | 89.3 | 1.231 | 8.27 | 2.5 | 4.7 | 101.78 | 0.968 | 45 |
| 4 | 5 | 0 | 11.10 | 90.7 | 1.334 | 8.36 | 2.4 | 4.4 | 100.55 | 0.956 | 45 |
| 5 | 5 | 0 | 11.08 | 90.6 | 1.237 | 8.30 | 2.4 | 4.5 | 100.91 | 0.966 | 45 |
| 6 | 10 | 0 | 11.05 | 87.6 | 1.117 | 8.40 | 2.4 | 4.3 | 101.31 | 0.955 | 45 |
| 7 | 10 | 0 | 11.07 | 88.8 | 1.169 | 8.34 | 2.5 | 4.2 | 100.99 | 0.964 | 45 |
| 8 | 10 | 0 | 11.10 | 88.4 | 1.081 | 8.31 | 2.5 | 4.4 | 101.53 | 0.958 | 45 |
| 9 | 15 | 0 | 11.02 | 86.4 | 0.977 | 8.28 | 2.4 | 4.5 | 101.32 | 0.961 | 45 |
| 10 | 15 | 0 | 11.05 | 87.5 | 1.029 | 8.31 | 2.5 | 4.4 | 101.81 | 0.945 | 45 |
| 11 | 15 | 0 | 11.08 | 87.6 | 1.044 | 8.35 | 2.4 | 4.3 | 100.7 | 0.961 | 45 |

|  | °T | Bact. | WPG | Visco. | ICI | pH | Gloss | Sheen | Tint | C/R | Foam |
|---|---|---|---|---|---|---|---|---|---|---|---|
| Control | RT | 3 | 11.16 | 92 | 1.3 | 8.63 | 1.9 | 4.5 | 99.22 | 0.947 | 11 |
| 12 | 45.5° C. | 0 | 11.09 | 91.8 | 1.15 | 8.22 | 1.8 | 4.0 | 101.17 | 0.947 | 13 |
| 13 | 74.4° C. | 0 | 11.09 | 92.1 | 1.08 | 8.12 | 1.8 | 3.7 | 102.15 | 0.945 | 20 |

The end notes for the Table in Example 10A are applicable to the Table in Example 10B.

Example 11

The experiments from Example 7 for paints without biocides are continued in this Example. Biocide free paint samples were made and tested free of biological agents using the HyCheck method described above. These paint samples are inoculated with 2% inoculum similar to those used above, and then incubated for two days at 25° C. to promote bacterial growth. The inoculated and incubated samples were tested and exhibited a rating of 4, i.e., very strong bacterial growth for an additional 24 hour testing period at 30° C.

Vials were filled with about 28 grams of the biocide free, inoculated paint samples. The vials are further incubated for 1, 2, 3, 6 or 7 days and then pasteurized in a hot water bath at 60° C., 65.5° C. and 72° C. for various time periods from 0.5 minute to 12 minutes, as shown in the table below. Control samples without pasteurization are also included for comparison. Levels of bacteria and mold were measured using the Hycheck tests and reported below.

| Incubation time (days) | | Bacteria Growth | | | | | Mold Growth | | | |
|---|---|---|---|---|---|---|---|---|---|---|
| ° C. | min:sec | 1 | 2 | 3 | 6 | 7 | 2 | 3 | 6 | 7 |
| 60 | 2:00 | 4 | 4 |  | 4 | 4 | 0 |  | 0 | 0 |
| 60 | 3:00 | 3 | 3 |  | 3 | 3 | 0 |  | 0 | 0 |
| 60 | 4:00 | 0.5 | 1 |  | 2 | 2 | 0 |  | 0 | 0 |
| 60 | 4:30 | 0 | 0 | 0 | 0 |  | 0 | 0 | 0 |  |
| 60 | 7:00 | 0 | 0 | 0 | 0 |  | 0 | 0 | 0 |  |
| 60 | 12:00 | 0 | 0 | 0 | 0 |  | 0 | 0 | 0 |  |
| 65.5 | 1:00 | 3 | 3 |  | 3 | 3 | 0 |  | 0 | 0 |
| 65.5 | 2:00 | 3 | 4 |  | 4 | 4 | 0 |  | 0 | 0 |
| 65.5 | 3:00 | 0.5 | 1 |  | 2 | 2 | 0 |  | 0 | 0 |
| 65.5 | 4:00 | 0 | 0 |  | 0 | 0 | 0 |  | 0 | 0 |
| 65.5 | 4:30 | 0 | 0 | 0 | 0 |  | 0 | 0 | 0 |  |
| 65.5 | 7:00 | 0 | 0 | 0 | 0 |  | 0 | 0 | 0 |  |
| 65.5 | 12:00 | 0 | 0 | 0 | 0 |  | 0 | 0 | 0 |  |
| 72 | 0:30 | 3 | 3 |  | 3 | 3 | 0 |  | 0 | 0 |
| 72 | 1:00 | 4 | 4 |  | 4 | 4 | 0 |  | 0 | 0 |
| 72 | 2:00 | 0 | 0 |  | 0 | 0 | 0 |  | 0 | 0 |
| 72 | 3:00 | 0 | 0 |  | 0 | 0 | 0 |  | 0 | 0 |
| 72 | 4:00 | 0 | 0 |  | 0 | 0 | 0 |  | 0 | 0 |
| 72 | 4:30 | 0 | 0 | 0 | 0 |  | 0 | 0 | 0 |  |
| 72 | 7:00 | 0 | 0 | 0 | 0 |  | 0 | 0 | 0 |  |
| 72 | 12:00 | 0 | 0 | 0 | 0 |  | 0 | 0 | 0 |  |
| None | n/a | 4 | 4 |  | 4 | 4 | 0 |  | 0 | 0 |

The results show that pasteurization by hot water bath at 60° C. is effective at about 4.5 minutes, at 65.5° C. is effective at about 4 minutes and at 72° C. is effective at about 2 minutes. Based on the tests conducted, the inventors believe that pasteurization at 65.5° C. can be reduced to about 3.5 minutes. The results from this Example 11 are compared to those from Example 7, which were pasteurized by heated air oven.

| Pasteurizing Time (min) | Temperature (° C.) | Pasteurized by |
|---|---|---|
| 2:00 | 72 | Hot water |
| 4:00 | 65.5 | Hot water |
| 4:30 | 60 | Hot water |
| 75:00 | 60 | Heated air oven |
| 360:00 | 49 | Heated air oven |

While the results from Example 7 appear to be different than those from Example 11, the inventors noted that Example 7 utilizes vials holding 52 grams of biocide free paints and Example 11 utilizes vials holding only 28 grams of biocide free paints.

The difference in the paint mass, i.e., 28 g versus 52 g, and the difference is pasteurization methods, i.e., hot water bath versus heated air oven, can account for this apparent difference between Examples 7 and 11. The specific heat capacity of air is 1,005 Joules/kg·° C. and the specific heat capacity of water is 4,186 Joules/kg·° C. The volume of 1 kg of dry air at sea level and at 15° C. is about 0.816 $m^3$ and the volume of 1 kg of water at sea level is only about 0.001 $m^3$. Hence, the informal "volumetric" heat capacity of air is 1,231 J/$m^3$·° C. and for water is 4,186,000 J/$m^3$·° C. In other words, the volumetric heat capacity of water is three orders of magnitude higher than that of air. The lag time in the air oven would be significantly longer than in a hot bath.

The inventors note that based on the results presented herein, pasteurization can be carried out by heated air, hot water bath, heated pipes or vessels that carry or transport the paints or other methods that can transfer heat to the paints. The present invention is not limited to any particular method of heat pasteurization.

While it is apparent that the illustrative embodiments of the invention disclosed herein fulfill the objectives stated above, it is appreciated that numerous modifications and other embodiments may be devised by those skilled in the art. One such modification is that paint may be heated to various elevated temperatures during production which includes the paint making mixing, processing, transfer and filling (of cans or other containers) steps and this exposure to elevated temperatures for various times as described above will pasteurize it. Therefore, it will be understood that the appended claims are intended to cover all such modifications and embodiments, which would come within the spirit and scope of the present invention.

We claim:
1. A method for pasteurizing a paint or stain composition comprising the steps of
   (i) preparing the paint or stain composition, wherein the paint or stain composition comprises latex particles that when applied to a substrate form a paint film;
   (ii) treating the paint or stain composition with a gamma radiation, wherein an amount of applied gamma radiation is less than about 15 kilograys without further polymerizing the paint or stain composition; and
   (iii) storing the treated paint or stain composition in containers.

2. The method of claim 1, wherein step (iii) comprises storing the pasteurized paint or stain composition at temperatures that discourages or inhibits growth of biological agents.

3. The method of claim 2, wherein said temperatures are temperatures below ambient temperature.

4. The method of claim 1, wherein the amount of applied gamma radiation ranges from about 3 kilograys to about 15 kilograys.

5. The method of claim 1, wherein the amount of applied gamma radiation ranges from about 5 kilograys to about 10 kilograys.

6. The method of claim 1, wherein the amount of applied gamma radiation ranges from about 3 kilograys to about 5 kilograys.

* * * * *